(12) United States Patent
Jencks et al.

(10) Patent No.: US 10,260,662 B2
(45) Date of Patent: Apr. 16, 2019

(54) LOW CARRYOVER HIGH PRESSURE FLUIDIC FITTING

(71) Applicant: Waters Technologies Corporation, Milford, MA (US)

(72) Inventors: Robert A. Jencks, Mendon, MA (US); Mark W. Moeller, Norton, MA (US); Kenneth R. Plant, Leominster, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 359 days.

(21) Appl. No.: 15/095,427

(22) Filed: Apr. 11, 2016

(65) Prior Publication Data

US 2016/0223108 A1 Aug. 4, 2016

Related U.S. Application Data

(62) Division of application No. 14/122,795, filed as application No. PCT/US2012/041220 on Jun. 7, 2012, now Pat. No. 9,334,989.

(Continued)

(51) Int. Cl.
*F16L 19/02* (2006.01)
*F16L 19/06* (2006.01)
*G01N 30/60* (2006.01)

(52) U.S. Cl.
CPC ......... *F16L 19/061* (2013.01); *F16L 19/0206* (2013.01); *F16L 19/0212* (2013.01); *F16L 19/06* (2013.01); *G01N 30/6026* (2013.01)

(58) Field of Classification Search
CPC ....... F16L 19/06; F16L 19/061; F16L 19/065; F16L 19/0206; F16L 19/0212

(Continued)

(56) References Cited

U.S. PATENT DOCUMENTS 1,912,299 A  5/1933  Parker
2,988,385 A  6/1961  Foelester et al.
(Continued)

FOREIGN PATENT DOCUMENTS

DE  102009022368 B3  11/2010
GB  2482175  1/2012
(Continued)

OTHER PUBLICATIONS

US 8,573,563 B1, 11/2013, Gamache (withdrawn)
(Continued)

*Primary Examiner* — Aaron M Dunwoody
(74) *Attorney, Agent, or Firm* — Schmeiser, Olsen & Watts LLP (57) ABSTRACT

Described is a fitting for coupling fluidic paths which facilitates secure and low leak rate fluid flow through a fluidic path junction such as a junction in a liquid chromatography system or other chemical analysis instrument. Fluid containing various mixtures of chemical samples can pass through the junction at high pressure with little or no trapped residue remaining in a volume at the connection. According to various embodiments, a face seal is achieved between two separate fluidic path features. In some embodiments, the sealing of the fluidic paths is aided by the use of a compliant polymer seal. The seal facilitates intimate contact between adjacent surfaces and significantly limits or prevents the entry of fluid under high pressure into an unswept volume. Thus the risk of carryover and its adverse effect on measurements is reduced or eliminated.

16 Claims, 8 Drawing Sheets

Related U.S. Application Data (60) Provisional application No. 61/498,664, filed on Jun. 20, 2011.

(58) Field of Classification Search
USPC .............................. 285/342, 353, 384, 385
See application file for complete search history.

(56) References Cited

U.S. PATENT DOCUMENTS

| | | |
|---|---|---|
| 3,434,744 A | 3/1969 | Yoke et al. |
| 3,485,517 A | 12/1969 | Howe |
| 4,026,803 A | 5/1977 | Abrahams et al. |
| 4,281,679 A | 8/1981 | Stearns |
| 4,619,473 A | 10/1986 | Someya |
| 4,690,437 A | 9/1987 | Anderson, Jr. |
| 5,120,084 A | 6/1992 | Hashimoto |
| 5,402,829 A | 4/1995 | Takikawa et al. |
| 5,423,581 A | 6/1995 | Salyers |
| 6,158,780 A | 12/2000 | Schaldach |
| 7,533,909 B2 | 5/2009 | Sausner et al. |
| 7,784,838 B2 | 8/2010 | Levy |
| 7,789,433 B2 | 9/2010 | Calnek |
| 7,909,367 B2 | 3/2011 | Plant et al. |
| 8,079,621 B2 | 12/2011 | Ferlin et al. |
| 8,696,038 B2 | 4/2014 | Nienhuls |
| 8,740,261 B2 | 6/2014 | Ford et al. |
| 9,751,085 B2 * | 9/2017 | Pa .................. B01L 3/5635 |
| 2003/0107216 A1 | 6/2003 | Gibson |
| 2004/0247255 A1 * | 12/2004 | Rosenburg ......... G02B 6/3825 |
| | | 385/78 |
| 2007/0158942 A1 | 7/2007 | Keene |
| 2011/0025047 A1 | 2/2011 | Zelechonok et al. |
| 2011/0107823 A1 * | 5/2011 | Dehmer ............. F16L 19/061 |
| | | 73/64.56 |
| 2013/0193683 A1 | 8/2013 | Seto et al. |
| 2013/0298647 A1 * | 11/2013 | Falk-Jordan ........ F16L 19/061 |
| | | 73/61.55 |
| 2014/0130580 A1 | 5/2014 | McAdams et al. |
| 2014/0196524 A1 | 7/2014 | Hirmer et al. |
| 2015/0300542 A1 * | 10/2015 | Graham ............. G01N 30/6026 |
| | | 285/393 |
| 2015/0308989 A1 | 10/2015 | Hochgraeber et al. |
| 2015/0369403 A1 * | 12/2015 | Cormier ............. G01N 30/6026 |
| | | 285/357 |
| 2018/0094753 A1 * | 4/2018 | Leveille .............. F16L 19/0206 |

FOREIGN PATENT DOCUMENTS

| | | |
|---|---|---|
| WO | 2004025162 | 3/2004 |
| WO | 2010000324 | 1/2010 |
| WO | 2010133192 | 11/2010 |
| WO | 2011076244 | 6/2011 |
| WO | 2012149930 A1 | 11/2012 |
| WO | 2013174421 A1 | 11/2013 |

OTHER PUBLICATIONS

Extended Search Report in European Patent Application No. 1720343.6, dated Feb. 16, 2018; 6 pages.

Partial Supplementary Search Report in related European Patent Application No. 12802451.0, dated Jan. 28, 2015; 8 pages.

International Search Report & Written Opinion in priority International Patent Application No. PCT/US12/41220, dated Aug. 6, 2012; 10 pages.

International Preliminary Report on Patentability in priority International Patent Application No. PCT/US12/41220, dated Jan. 9, 2014; 9 pages.

Extended Search Report in counterpart European Patent Application No. 16186225.5, dated Dec. 19, 2016; 6 pages.

* cited by examiner

FIG. 1

PRIOR ART

LOW CARRYOVER HIGH PRESSURE FLUIDIC FITTING

RELATED APPLICATION

This application is a divisional of U.S. patent application Ser. No. 14/122,795, filed Nov. 27, 2013, titled "Low Carryover High Pressure Fluidic Fitting," which is the national stage of International Application No. PCT/US12/41220, filed Jun. 7, 2012, titled "Low Carryover High Pressure Fluidic Fitting," which claims the benefit of the earlier filing date of U.S. Provisional Patent Application Ser. No. 61/498,664, filed Jun. 20, 2011, titled "Low Carryover High Pressure Fluidic Fitting," the entireties of which are incorporated herein by reference.

FIELD OF THE INVENTION

The invention relates generally to fluidic couplings for high pressure systems. More particularly, the invention relates to leak tight fluidic couplings with near zero unswept volume for liquid chromatography systems.

BACKGROUND

Chemical analysis systems can include fluidic paths that accommodate high pressures. For example, a liquid chromatography system, such as a system designed for ultra high performance liquid chromatography (UHPLC), can operate at pressures of 15,000 psi or greater. The fluidic paths in such systems often include tubing that is coupled to other components or tubing using a conventional coupling such as a standard compression fitting.

In general, several requirements exist to maintain suitable performance of the chemical analysis system. First, a secure fluidic seal between the coupled elements is required at a low leak rate determined by the desired performance of the chemical analysis system. In addition, the fluidic seal should be sufficiently stable to prevent the release and re-uptake of fluid containing chemical samples or mixtures of samples through the seal interface. Re-uptake can result in carryover, which can significantly degrade system performance. Finally, the unswept volume, or the physical space within the fluid path in which fluid can be trapped and not flushed out by fluid flow, should be minimized. Unswept volume typically occurs between the end of the tubing and the point of seal on a ferrule further back in the fitting assembly. Excessive unswept volume can also result in carryover.

SUMMARY

In one aspect, the invention features a fitting for coupling fluidic paths and includes a coupling body, compression screw, tube assembly, collet and polymer seal. The coupling body has a threaded bore, a first bore and a second bore for receiving the tube assembly. The first bore extends from an end of the threaded bore and the second bore extends from an end surface of the first bore. The second bore has a diameter that is less than a diameter of the first bore and has a sealing surface at an end opposite to the first bore with a channel extending from the sealing surface to pass a fluid. The compression screw has an axial bore, a threaded portion in engagement with the threaded bore of the coupling body and a drive surface. The tube assembly has a sleeve and a tube disposed through the sleeve. The tube has an endface and is secured to the sleeve proximate to the endface. A portion of the tube that includes the endface protrudes from the sleeve. The tube assembly extends through the axial bore of the compression screw. The collet is secured to an outer surface of the sleeve and has a first end configured to receive the drive surface of the compression screw and a second end. The polymer seal has a lower seal portion and an upper seal portion. The lower seal portion has a channel to pass a fluid and a diameter substantially the same as the diameter of the second bore. The upper seal portion has an opening to receive an end of the tube assembly and has a diameter substantially the same as the diameter of the first bore. A fluidic seal is formed between the endface of the tube and the sealing surface of the second bore by the polymer seal when the second end of the collet is in contact with the upper seal portion of the polymer seal.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a tube fitting and connection system to facilitate secure, low leak rate fluid flow through a junction of fluidic paths in a chemical analysis instrument such as a liquid chromatography system. The device allows fluid containing various mixtures of chemical samples to pass through the junction of the fluidic paths at high pressure with little or no trapped residue remaining in the connection. Trapped residue is an undesirable condition present in many high pressure liquid connections and can lead to degradation in performance of the analytical instrument. According to various embodiments, the device provides a face seal between two separate fluidic path features. Fluidic paths can be in the form of cylindrical tubes or passages drilled or otherwise created in solid structures for the management of fluid. Sealing of fluidic paths can be aided by the use of compliant polymer seals which facilitate intimate contact between adjacent surfaces. Intimate contact significantly limits or prevents the entry of fluids under high pressure into volumes that are not directly in the fluid flow. Thus the risk of a fluid, such as a chemical sample, entering an unswept or trapped volume near the sealing features is reduced or eliminated.

Figure 1:
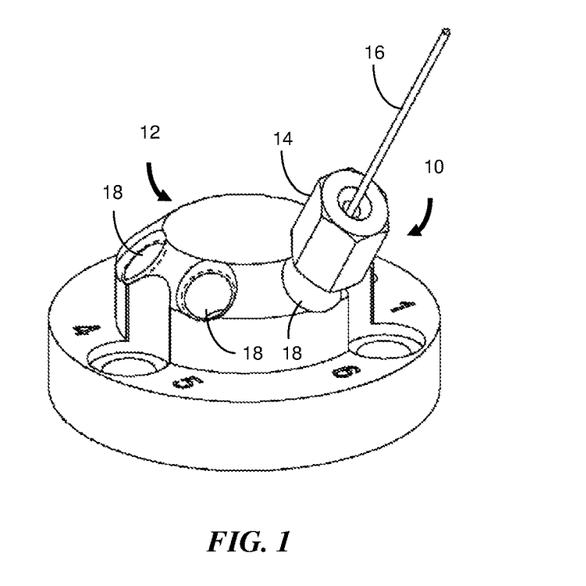
FIG. 1 is an illustration of a fluidic coupling for a rotary shear seal valve in a liquid chromatography system.

By way of example, FIG. 1 shows a view of a fluidic coupling 10 at the interface of a sample loop and a stator portion 12 of a rotary shear seal valve for a liquid chromatography system. The coupling 10 includes a compression nut 14 and other components (not visible). A tube 16 defines a fluidic path that conducts a fluid from a sample source to a stator port 18 at the coupling 10 or from the stator port 18 to a chromatographic column. A second fluidic path is present inside the stator portion 12 and interfaces with a rotor that couples, or decouples, the second fluidic path with another fluidic path that communicates with one of the other stator ports 18.

Figure 2A:
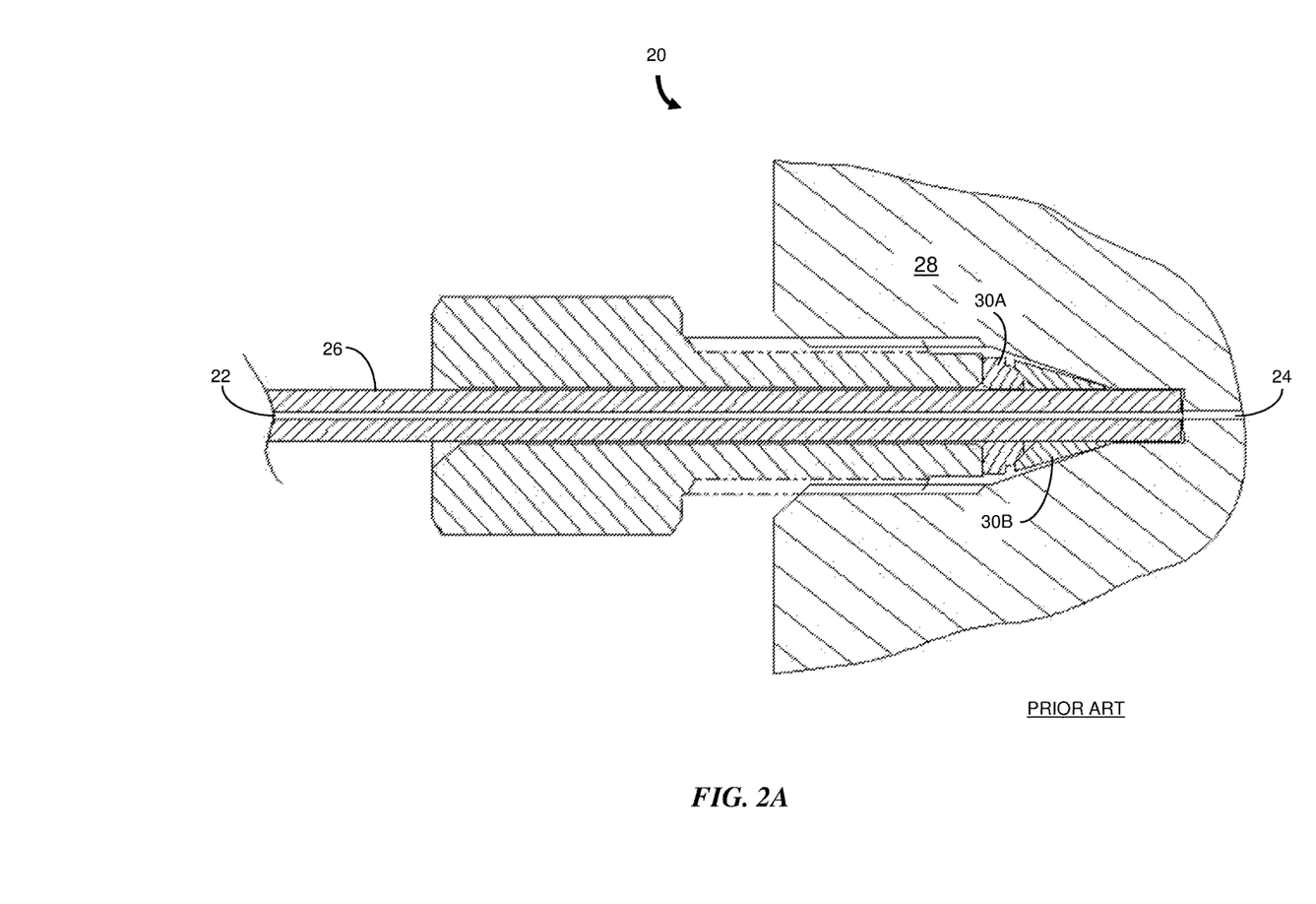
FIG. 2A a cross-sectional view of a conventional compression fitting for coupling two fluidic paths.
Figure 2B:
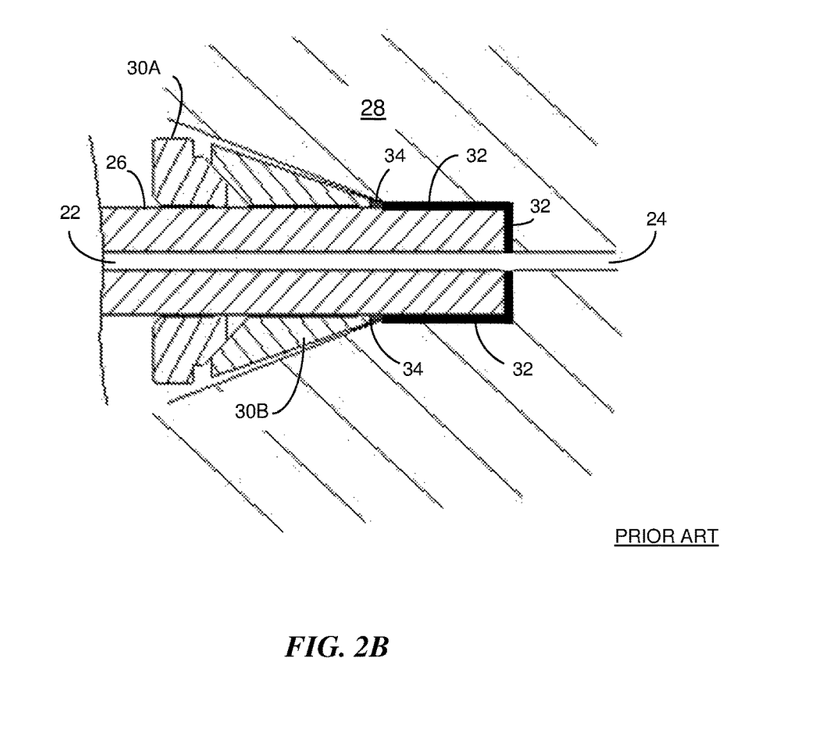
FIG. 2B is an expanded view of a portion of FIG. 2A that shows the sealing interface.

FIG. 2A shows a cross-sectional view of a conventional fitting 20 that can be used, for example, to couple two fluidic paths 22 and 24. For example, the fitting 20 can be used to couple the tube 16 of FIG. 1 to an internal fluidic path in the rotary shear seal valve. Tube 26 includes the first fluidic path 22 which is coupled to the second fluidic path 24 at a bottom surface of a coupling body 28. FIG. 2B is an expanded view of a portion of FIG. 2A that shows the sealing interface. A two-part ferrule 30A and 30B engages an inner tapered surface of the coupling body 28 and the outer diameter of the tube 26. The resulting fluidic seal can withstand a high fluid pressure (e.g., greater than 15,000 psi); however, an unswept volume (designated by the thick black lines 32 and the region to the right of the contact zone 34 between ferrule part 30B and the tapered surface) can exist and may result in sample carryover. For example, as the sample moves past the unswept volume 32, some of the sample may diffuse into the volume 32. The sample in the unswept volume 32 can subsequently diffuse back into the main fluid flow in fluidic path 24. If the fitting 20 is used with components of a liquid chromatography system, such as illustrated in FIG. 1, the fluid sample that diffuses back into the fluid flow (i.e., the carryover) can adversely affect chromatographic results.

Figure 3A:
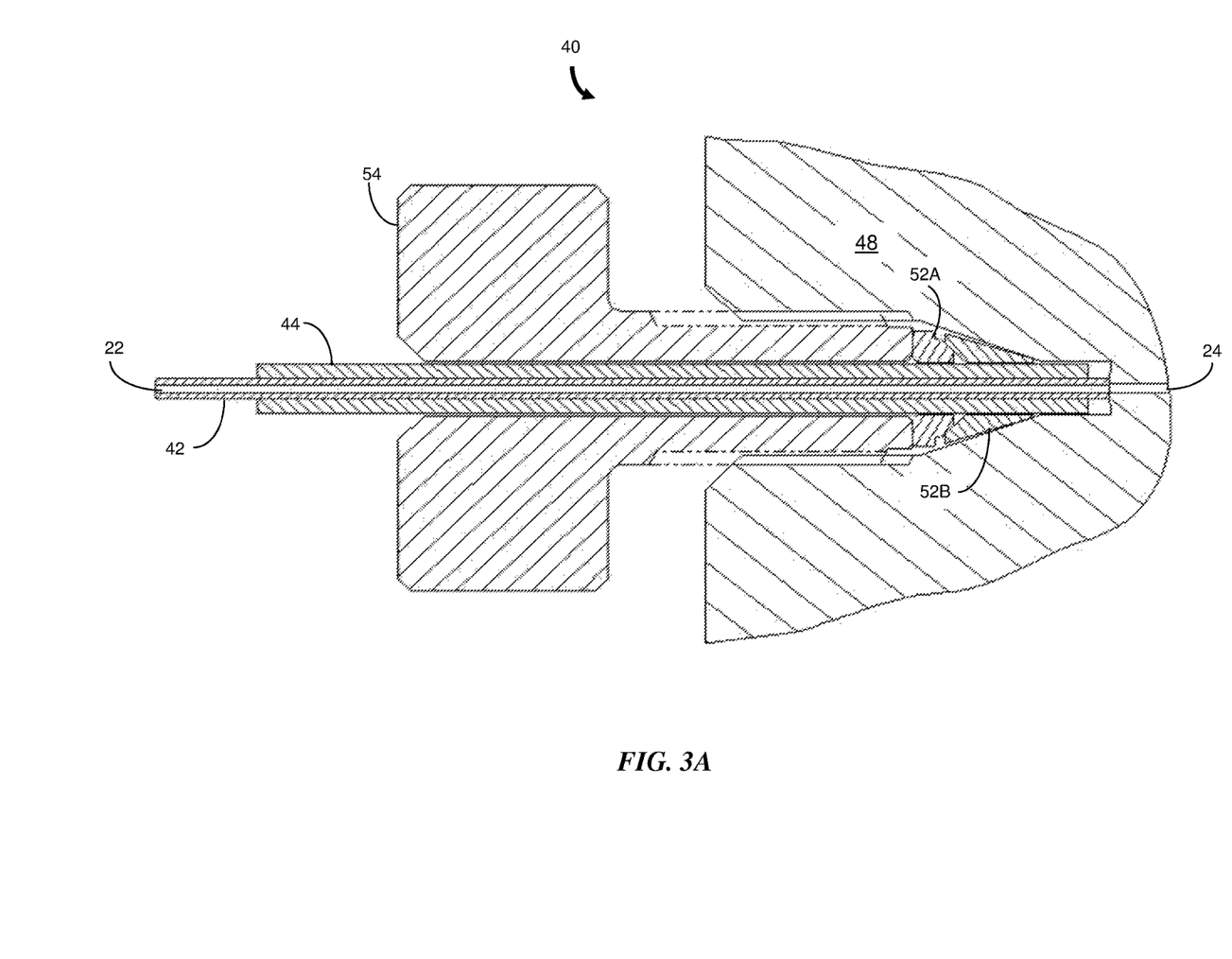
FIG. 3A is a cross-sectional view of a fitting for coupling fluidic paths according to an embodiment of the invention.
Figure 3B:
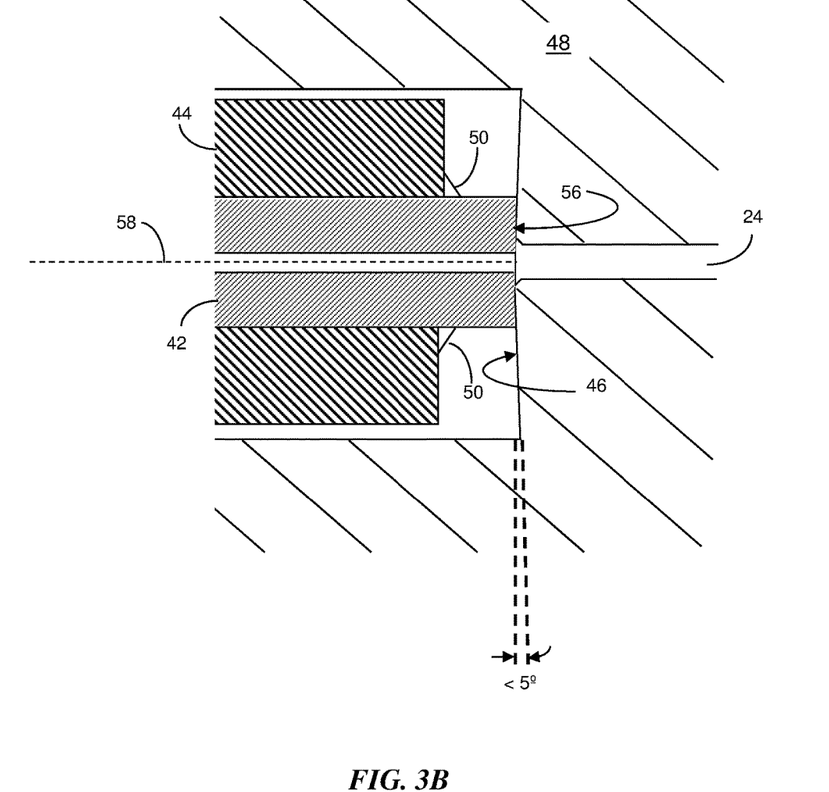
FIG. 3B is an expanded cross-sectional view of the fitting of FIG. 3A in a region of the face seal.

FIG. 3A is a cross-sectional view of an embodiment of a fitting 40 for coupling fluidic paths according to the invention. FIG. 3B is an expanded cross-sectional view of the fitting 40 in a region where a face seal is created. The fitting 40 includes a tube assembly having a stainless steel tube 42 surrounded over a portion of its length by a stainless steel sleeve 44. The tube 42 and sleeve 44 are joined at the end of the sleeve 44 with the tube 42 protruding a sufficient length (e.g., 0.015 in.) to allow it to contact a sealing surface 46 of a coupling body 48. In a preferred embodiment, the tube 42 and sleeve 44 are joined by a weld 50. The weld 50 may be, for example, a laser weld or an electron beam weld as are known in the art. By way of a specific dimensional example, the inner and outer diameters of the stainless steel tube 42 can be 0.004 in. and 0.025 in., respectively, the outer diameter of the sleeve 44 can be 0.062 in. and the diameter of the second fluid path 24 in the coupling body 48 can be 0.006 in.

The tube assembly is encircled by a two-part compression member 52A and 52B (generally 52) in a tapered cavity of the coupling body 48. For example, the compression member 52 can be a stainless steel ferrule set (e.g., part no. SS-100-SET available from Swagelok Company of Solon, Ohio). A compression screw 54 having threads that engage threads in an upper portion of the coupling body 48 is used to force the compression member 52 against the surface of the tapered cavity. The force causes the compression member 52 to grip the sleeve 44 and force the tube assembly into intimate contact with the sealing surface 46 of the coupling body 48. Preferably, the sealing surface 46 has a weak conical form (e.g., the surface 46 departs from a flat surface by less than) 5° to thereby reduce the surface area of the end face 56 of the stainless steel tube 42 that contacts the sealing surface 46. The end face 56 of the stainless steel tube 42 is substantially normal to the longitudinal axis 58 of the tube 42 and has a low surface roughness (e.g., flat to within 0.000032 in.). As long as the compression screw 54 maintains forceful contact with the compression member 52, and therefore the tube assembly, a tight fluid seal is maintained between the end face 56 of the protruding tube 42 and the sealing surface 46 of the coupling body 48.

Figure 4:
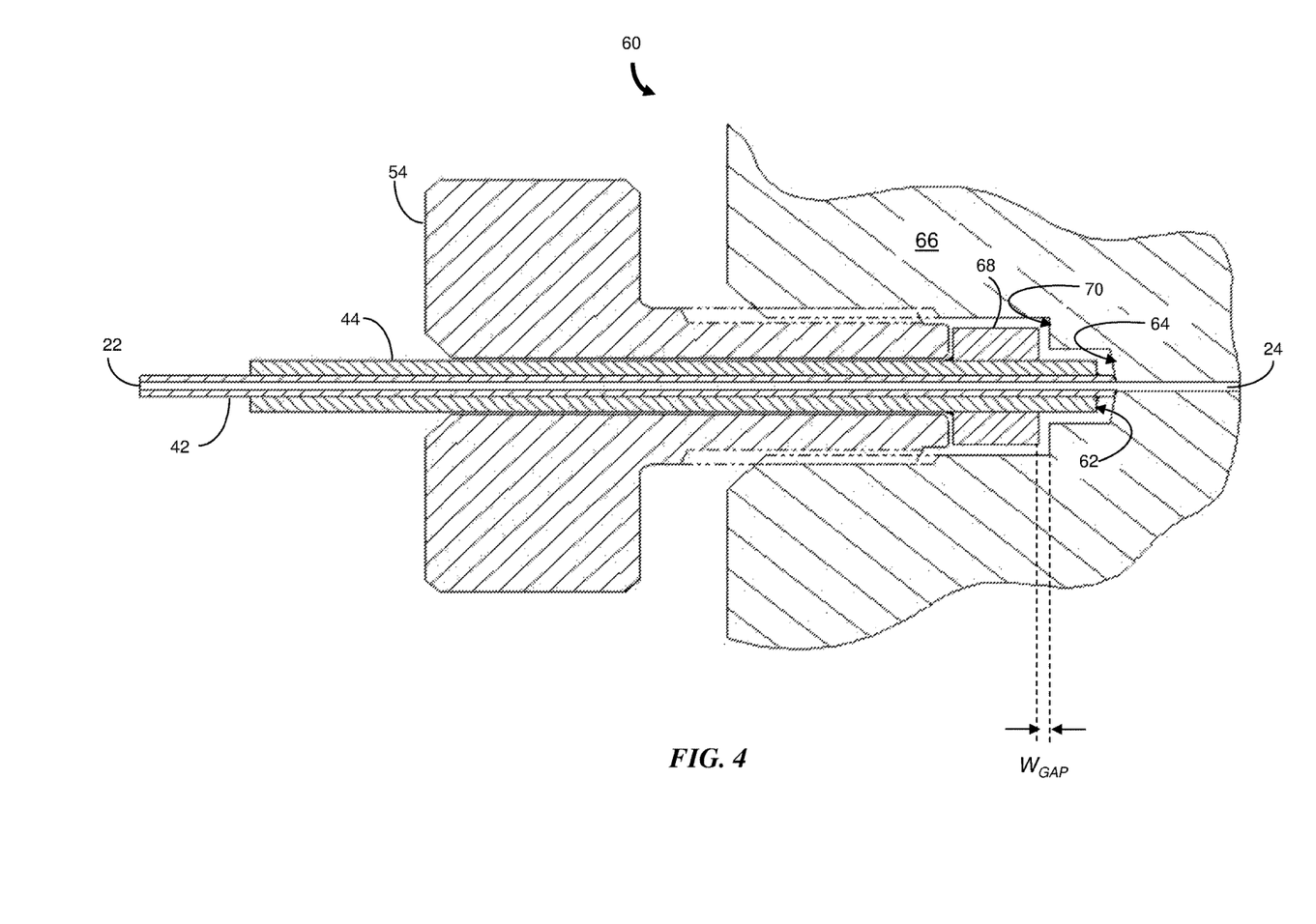
FIG. 4 is a cross-sectional view of a fitting for coupling fluidic paths according to another embodiment of the invention.

FIG. 4 is a cross-sectional view of a fitting 60 according to another embodiment of the invention. The fitting 60 includes a stainless steel tube assembly similar to that shown in FIGS. 3A and 3B. The end face 62 of the stainless steel tube 42 is tapered to form a shallow male cone which engages a female cone of slightly different angle formed in the sealing surface 64 of the coupling body 66. Although other cone angles are possible, by way of a specific numerical example, the shallow male cone can have a cone angle of 139° and the cone angle of the sealing surface 64 can be 140°.

A collet 68, or bushing, is attached to the outer surface of the stainless steel sleeve 44 by welding or other suitable attachment method. A threaded compression screw 54 engages threads in the coupling body 66 to apply compressive force to the tube assembly by means of the attached collet 68. The compressive force urges the tapered end face 62 of the stainless steel tube 42 against the tapered sealing surface 64 of the coupling body 66. The force is sufficient to create and maintain intimate contact between the end face 62 and sealing surface 64, thereby creating a secure fluidic seal. A bore end surface 70 at one end of a larger bore of the coupling body 66 is configured to receive an end of the welded collet 68. Once the compression screw 54 is rotated sufficiently so that the welded collet 68 traverses an initial gap of width WGAP and makes contact with the bore end surface 70, the subsequent resistance encountered prevents a user from further tightening the compression screw 54. This restriction prevents damage to the tapered end face 62, protruding portion of the stainless steel tube 42 and the tapered sealing surface 64 that might otherwise occur to the effectiveness of the fluidic seal.

In various embodiments, the taper angle and size of the formed end face 62 can be adjusted to obtain a suitable contact at the interface of the end face 62 and the sealing surface 64 of the coupling body 66 to achieve an acceptable fluidic seal for varying conditions of pressure and flow.

Figure 5A:
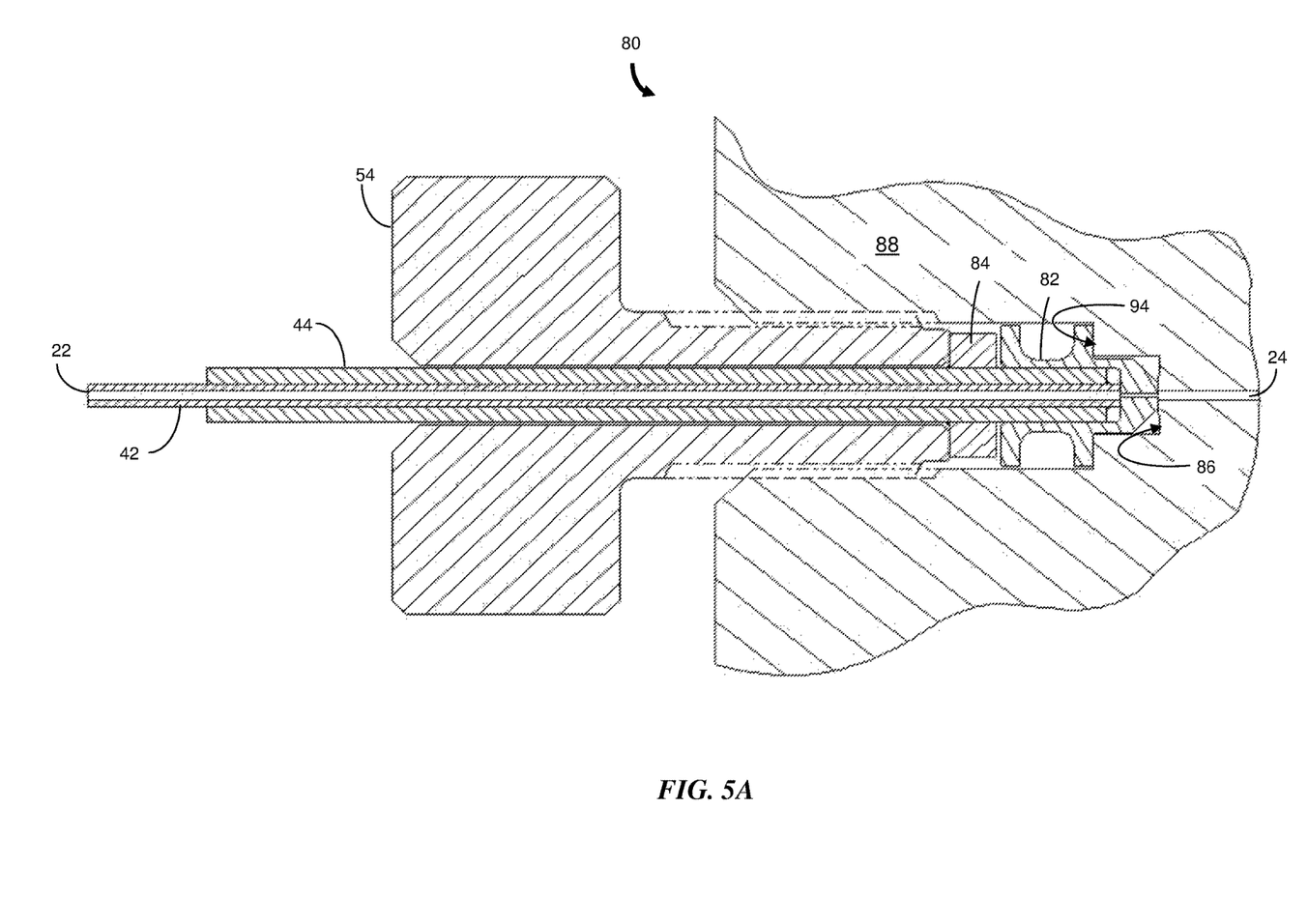
FIG. 5A is a cross-sectional view of a fitting for coupling fluidic paths according to another embodiment of the invention.
Figure 5B:
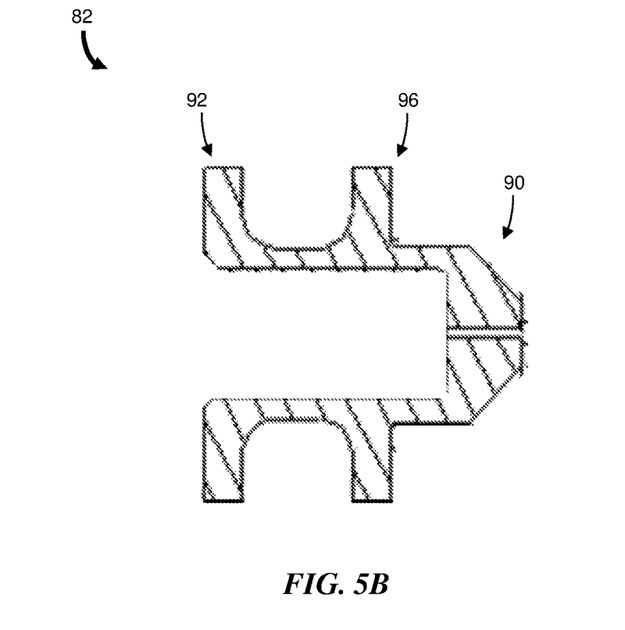
FIG. 5B is a detailed illustration of the polymer seal in the fitting of FIG. 5A.

FIG. 5A is a cross-sectional view of a fitting 80 according to another embodiment of the invention. The fitting 80 has a similar configuration to the fitting of FIG. 4; however, a polymer seal 82 (or polymer gasket), shown in more detail in FIG. 5B, is provided to encircle and substantially enclose the end of the tube assembly. The polymer seal 82 includes a lower seal portion 90 and first and second upper seal portions 92 and 96. The lower seal portion 90 has a smaller diameter than the upper seal portions 92, 96.

During insertion of the tube assembly into the coupling body 88, an initial gap exists between the end of the lower seal portion 90 and a sealing surface 86 of the narrow bore. As the compression screw 54 is turned, the polymer seal is 82 urged forward into the coupling body 88 to close the gap and then to engage the sealing surface 86. Additional rotation of the compression screw 54 compresses the lower seal portion 90 so that it conforms to the end of the stainless steel tube 42 and the sealing surface 86 to create a secure fluidic seal. Once the collet engages the first upper seal portion 92, further rotation urges the tube assembly, collet 84 and polymer seal 82 deeper into the coupling body 88 until the second upper seal portion 96 comes into contact with a bottom surface 94 of a larger bore. The upper seal portions 92, 96 are larger in dimension and therefore less compliant and allow only a small amount of additional compressive deformation of the polymer seal 82. Thus further rotation of the compression screw 54 is resisted and the bottom surface 94 of the larger bore acts as a stop to limit the amount of force applied to the stainless steel tube 42 and the sealing surface 86 of the narrow bore. Advantageously, the total fitting force applied by the compression screw 54 does not overload the seal interface and the polymer seal 82.

In various embodiments, the shape, angle and size of the polymer seal 82 features are modified to obtain a suitable seal interface under varying conditions of pressure and flow. The polymer material may be selected to provide suitable mechanical properties and chemical compatibility. In one embodiment, the polymer seal 82 is a Dupont Vespel® SCP-5000 polyimide gasket.

Alternative embodiments to the illustrated fitting 80 are contemplated. For example, one such embodiment utilizes a one-piece "plain tube" (i.e., a tube without a sleeve) having a tapered end face in place of the welded tube assembly.

Figure 6A:
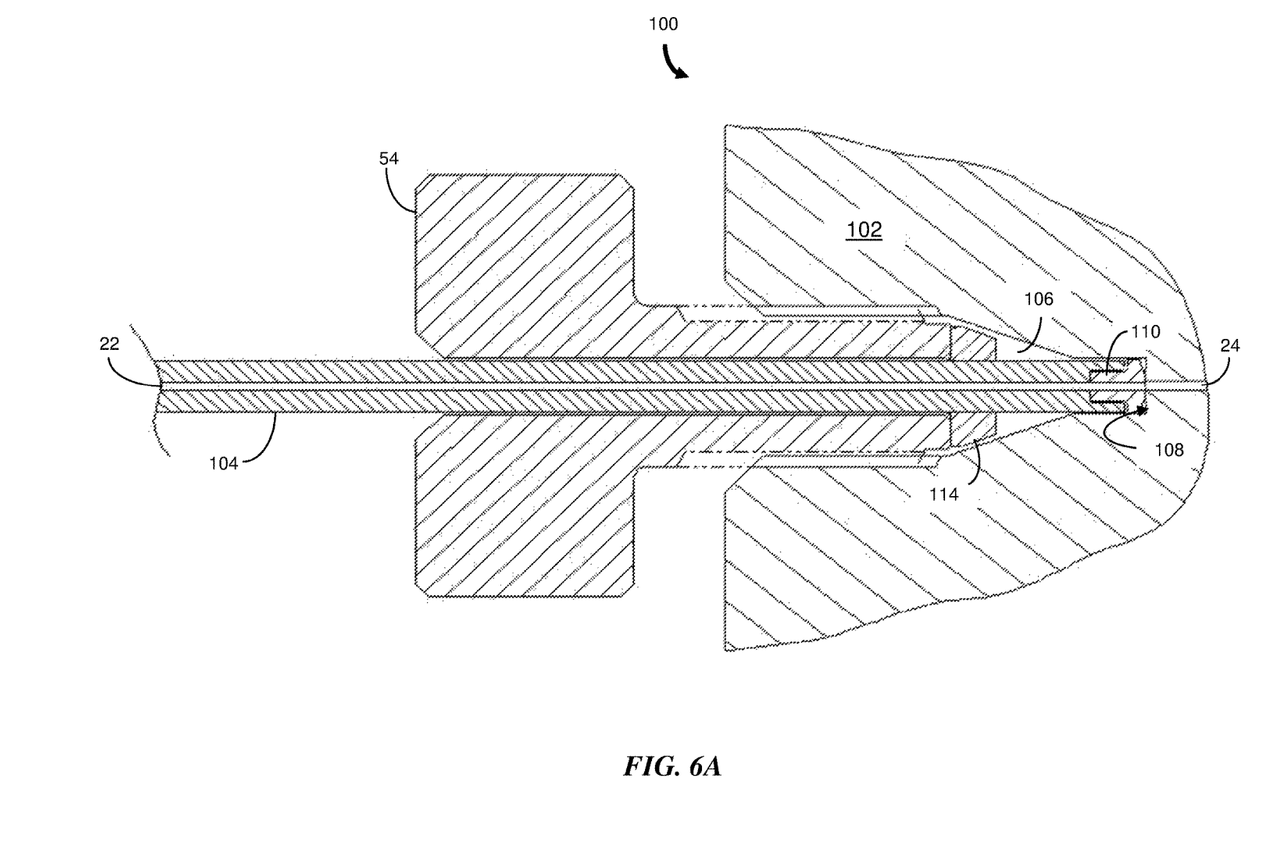
FIG. 6A is a cross-sectional view of a fitting for coupling fluidic paths according to another embodiment of the invention.

FIG. 6A is a cross-sectional view of a fitting 100 according to another embodiment of the invention. The fitting 100 includes a coupling body 102 having a threaded bore that receives a compression screw 54. The threaded bore opens into a tapered cavity 106. A narrow bore extending from the narrow end of the tapered cavity 106 includes a flat sealing surface 108. A single piece stainless steel tube 104 includes the fluidic channel 22 to be coupled to the fluidic channel 24 in the coupling body 102. The stainless steel tube 104 includes a pocket of depth D formed at its sealing end occupied by part of a stem portion of length L of a polymer seal 110.

Figure 6B:
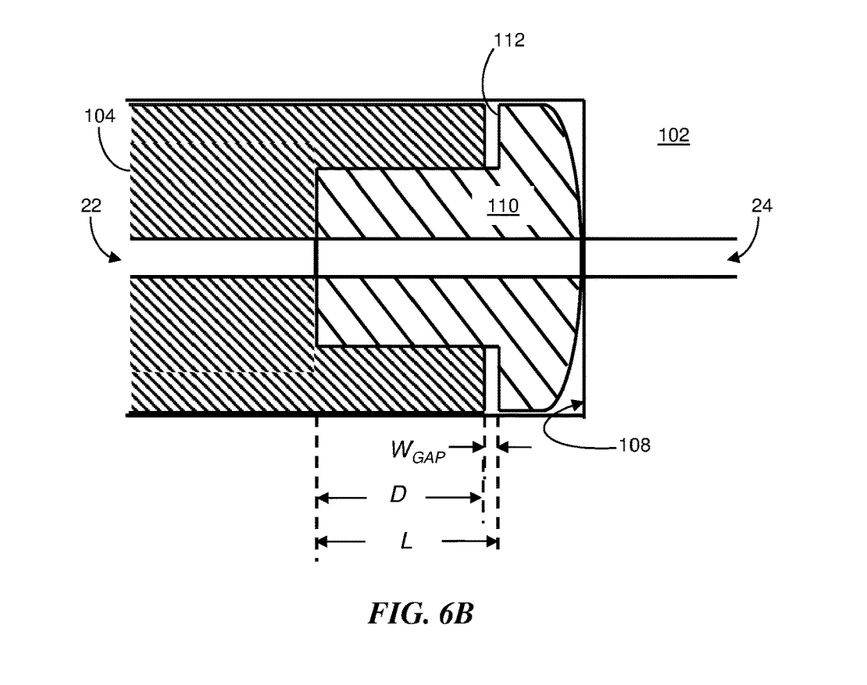
FIG. 6B is an illustration showing an expanded view of the sealing interface region of FIG. 6A.

FIG. 6B shows an expanded view of the region in which the fluidic paths 22, 24 are coupled. Referring to FIG. 6A and FIG. 6B, the polymer seal 110 is shaped so that when inserted without compression into the pocket, an initial gap of width WGAP exists between the end of the tube 104 and a flange portion 112 of the seal 110. The flange portion 112 extends radially outward to the outer diameter of the tube 104. A collet 114 having a tapered surface is secured to the tube 104 by welding or other appropriate attachment method. A threaded compression screw 54 is used to apply a compressive force to the tube 104 by means of a threaded bore in the coupling body 102 and the attached collet 112 in a manner similar to that described in the above embodiments. As the force is applied, the polymer seal 110 is pushed into intimate contact with the sealing surface 108 to create a secure fluidic seal. The initial gap between the end of the tube 104 and the flange portion 112 allows the polymer seal 110 to compress by an amount sufficient to create the fluidic seal. After sufficient force is applied to compress the polymer seal 110 and eliminate the gap, further force causes the end of the tube 104 to come into contact with the less compliant flange portion 112. Thus only a small amount of additional compressive deformation of the polymer seal 110 occurs at a much lower deformation rate and higher force level. As a result, the total force that can be applied to the sealing end of the stainless steel tube 104 is limited, ensuring that the total fitting force applied by the compression screw 54 does not overload the polymer seal 110 and damage the sealing surface 108.

In other embodiments, the shape and dimensions of the features of the polymer seal 110 are modified to obtain a suitable fluidic seal under varying conditions of pressure and flow. The polymer material can be selected to provide suitable mechanical properties and chemical compatibility. In one embodiment, the polymer seal 110 is a Dupont Vespel® SCP-5000 polyimide gasket.

While the invention has been shown and described with reference to specific embodiments, it should be understood by those skilled in the art that various changes in form and detail may be made therein without departing from the spirit and scope of the invention as recited in the accompanying claims.

What is claimed is:

1. A fitting for coupling fluidic paths, comprising:
a coupling body having a threaded bore, a first bore and a second bore for receiving a tube assembly, the first bore extending from an end of the threaded bore and the second bore extending from an end surface of the first bore, the second bore having a diameter that is less than a diameter of the first bore and having a sealing surface at an end opposite to the first bore with a channel extending from the sealing surface to pass a fluid;
a compression screw having an axial bore, a threaded portion in engagement with the threaded bore of the coupling body and a drive surface;
a tube assembly having a sleeve and a tube disposed through the sleeve, the tube having an endface and being secured to the sleeve proximate to the endface, wherein a portion of the tube that includes the endface protrudes from the sleeve, the tube assembly extending through the axial bore of the compression screw;
a collet secured to an outer surface of the sleeve and having a first end configured to receive the drive surface of the compression screw and a second end; and
a polymer seal having a lower seal portion and an upper seal portion, the lower seal portion having a channel to pass a fluid and a diameter substantially the same as the diameter of the second bore, the upper seal portion having an opening to receive an end of the tube assembly and having a diameter substantially the same as the diameter of the first bore, wherein the lower seal portion is configured to rest within the second bore and includes a lower seal surface configured to contact the sealing surface of the second bore, wherein a fluidic seal is formed between the endface of the tube and the sealing surface of the second bore by the polymer seal when the second end of the collet is in contact with the upper seal portion of the polymer seal such that the lower seal portion is disposed between the endface of the tube and the sealing surface of the second bore.

2. The fitting of claim 1 wherein a diameter of the first bore is equal to a diameter of the threaded bore.

3. The fitting of claim 1 wherein the tube is a stainless steel tube and the sleeve is a stainless steel sleeve.

4. The fitting of claim 1 wherein the tube assembly comprises a weld at an interface of the sleeve and the tube.

5. The fitting of claim 1 wherein the upper seal portion comprises a first upper seal portion and a second upper seal portion each having a diameter substantially the same as the diameter of the second bore, the first and second upper seal portions being separated from each other by a region of the upper seal portion having a diameter that is less than the diameters of the first and second upper seal portions.

6. The fitting of claim 1 wherein the polymer seal is formed of a polyimide material.

7. The fitting of claim 1, where the threaded bore, the first bore and the second bore extend into the coupling body in a first direction, and wherein the end surface of the first bore extends perpendicular to the first direction.

8. The fitting of claim 1, wherein the upper seal portion is configured to rest within the first bore and includes an upper seal surface configured to contact the end surface of the first bore.

9. A fitting for coupling fluidic paths, comprising:
a coupling body having a threaded bore, a first bore and a second bore for receiving a tube assembly, the threaded bore, the first bore and the second bore extending into the coupling body in a first direction, the first bore extending in the first direction from an end of the threaded bore and the second bore extending in the first direction from an end surface of the first bore, the end surface of the first bore extending perpendicular to the first direction, the second bore having a diameter that is less than a diameter of the first bore and having a sealing surface at an end opposite to the first bore with a channel extending from the sealing surface to pass a fluid, the sealing surface extending perpendicular to the first direction;
a compression screw having an axial bore, a threaded portion configured to engage with the threaded bore of the coupling body, and a drive surface;
a tube having an endface configured to extend through the axial bore of the compression screw,
wherein the tube includes an inner tube and an outer sleeve;
a collet configured to be secured to an outer surface of the sleeve and having a first end configured to receive the drive surface of the compression screw and a second end; and
a polymer seal having a lower seal portion and an upper seal portion, the lower seal portion having a channel to pass a fluid and a diameter substantially the same as the diameter of the second bore, the upper seal portion having an opening to receive an end of the tube assembly and having a diameter substantially the same as the diameter of the first bore, wherein the lower seal portion is configured to rest within the second bore and includes a lower seal surface configured to contact the sealing surface of the second bore, and wherein the upper seal portion is configured to rest within the first bore and includes an upper seal surface configured to contact the end surface of the first bore,
wherein a fluidic seal is formed between the endface of the tube and the sealing surface of the second bore by the polymer seal when the second end of the collet is in contact with the upper seal portion of the polymer seal such that the lower seal portion is disposed between the endface of the tube and the sealing surface of the second bore.

10. The fitting of claim 9, where the threaded bore, the first bore and the second bore extend into the coupling body in a first direction, and wherein the end surface of the first bore extends perpendicular to the first direction.

11. The fitting of claim 9, wherein the upper seal portion is configured to rest within the first bore and includes an upper seal surface configured to contact the end surface of the first bore.

12. A fitting for coupling fluidic paths, comprising:
a coupling body having a threaded bore, a first bore and a second bore for receiving a tube assembly, the threaded bore, the first bore and the second bore extending into the coupling body in a first direction, the first bore extending in the first direction from an end of the threaded bore and the second bore extending in the first direction from an end surface of the first bore, the end surface of the first bore extending perpendicular to the first direction, the second bore having a diameter that is less than a diameter of the first bore and having a sealing surface at an end opposite to the first bore with a channel extending from the sealing surface to pass a fluid, the sealing surface extending perpendicular to the first direction;
a compression screw having an axial bore, a threaded portion configured to engage with the threaded bore of the coupling body;
the tube assembly having an endface configured to extend through the axial bore of the compression screw; and
a polymer seal having a lower seal portion and an upper seal portion, the lower seal portion having a channel to pass a fluid and a diameter substantially the same as the diameter of the second bore, the upper seal portion having an opening to receive an end of the tube assembly and having a diameter substantially the same as the diameter of the first bore, wherein the lower seal portion is configured to rest within the second bore and includes a lower seal surface configured to contact the sealing surface of the second bore, and wherein the upper seal portion is configured to rest within the first bore and includes an upper seal surface configured to contact the end surface of the first bore,
wherein the polymer seal is configured to be disposed between the endface of the tube assembly and the sealing surface of the second bore such that a seal is formable between the endface of the tube and the sealing surface of the second bore.

13. The fitting of claim 12, further comprising a collet configured to be secured to an outer surface of the sleeve and having a first end configured to receive the drive surface of the compression screw and a second end.

14. The fitting of claim 12, where the threaded bore, the first bore and the second bore extends into the coupling body in a first direction, and wherein the end surface of the first bore extends perpendicular to the first direction.

15. The fitting of claim 12, wherein the upper seal portion is configured to rest within the first bore and includes an upper seal surface configured to contact the end surface of the first bore.

16. The fitting of claim 12, wherein the tube assembly includes an inner tube and an outer sleeve.

\* \* \* \* \*